United States Patent [19]
Schwartz et al.

[11] Patent Number: 5,954,636
[45] Date of Patent: Sep. 21, 1999

[54] PEDIATRIC ENDOTRACHEAL TUBE WITH BRONCHIAL BLOCKER AND METHOD FOR SELECTIVELY BLOCKING RESPIRATORY AIRFLOW TO A PEDIATRIC PATIENT'S LUNG

[76] Inventors: Roy E. Schwartz; Raymond K. Balsara, both of St. Christopher's Hosp., Phila., Pa. 19134

[21] Appl. No.: 08/893,010

[22] Filed: Jul. 15, 1997

[51] Int. Cl.$^6$ ...................................................... A61B 1/04
[52] U.S. Cl. ............................................................ 600/120
[58] Field of Search ................................... 600/114, 115, 600/116, 120, 144; 128/207.14, 207.17, 207.18, 206.26, 328, 341, 345, 343, 657

[56] References Cited

U.S. PATENT DOCUMENTS 3,599,642  8/1971  Tindel .
3,754,554  8/1973  Felberg .

(List continued on next page.)

OTHER PUBLICATIONS

"Univent—The New Concept For One Lung Anesthesia", Fuji Systems Corporation, undated.
"A New Tube for Single Lung Ventilation", Shreekant V. Karwande, M.D., *Chest,* Issue 92/4, Oct., 1987, pp. 761–763.
"Selective Endobronchial Intubation in Paediatrics: The Marraro Paediatric Bilumen Tube", Giuseppe Marraro, M.D., Paediatric Anaesthesia 1994, pp. 255–258.
"The Univent Tube is The Best Technique For Providing One–Lung Ventilation", James M. Gayes, M.D., and Peter Slinger, M.D., F.R.C.P.C., *Journal of Cardiothoracic and Vascular Anesthesia,* vol. 7, No. 1, Feb., 1993, pp. 103–112.
"Exsanguinating Hemoptysis", Antonio A. Garzon, M.D. et al., *J. Thorac Cardiovasc Surg,* 1982, pp. 829–833.
"Selective Pulmonary Suctioning Using a Tip Deflecting Wire in Mechanically Ventilated Patients", Jose E. Irazuzta, M.D., Critical Care Medicine, 1995, pp. 410–411.

"Lobar Bronchial Blockade in Bronchopleural Fistula", Zdenek Otruba, M.D. and Donald Oxorn, M.D., C.M., F.R.C.P.C., Canadian Journal of Anaesthesia, 1992, pp. 176–178.
"Use of Fiberoptic Bronchoscope to Assist Placement of a Fogarty Catheter as a Bronchial Blocker", Donald Oxorn, M.D., C.M., F.R.C.P.C., *Canadian Journal of Anaesthesia,* undated, pp. 427–428.
"The Urinary Catheter as a Bronchial Blocker", I.D. Conacher, *Anaesthesia,* vol. 38, 1983, pp. 475–477.
"Airway Management During Anesthesia for Double–Lung Transplantation Using a Single–Lumen Endotracheal Tube with an Enclosed Bronchial Blocker", Mark S. Scheller, M.D. et al., *Journal of Cardiothoracic and Vascular Anesthesia,* vol. 6, No. 2, Apr., 1992, pp. 204–207.
"New Device for One–Llung Anesthesia: Endotracheal Tube with Movable Blocker", Hiroshi Inoue, M.D. et al., *The Journal of Thoracic and Cardiovascular Surgery,* vol. 83, No. 6, Jun., 1982, pp. 940–942.

(List continued on next page.)

*Primary Examiner*—Beverly M. Flanagan
*Attorney, Agent, or Firm*—Charles N. Quinn

[57] ABSTRACT

Apparatus and method for selectively blocking respiratory airflow to a pediatric lung or a single lobe thereof. The apparatus comprises an endotracheal tube adapted for passage of a bronchoscope therethrough and a second flexible tube which is parallel with and fixedly contacting said endotracheal tube. A bronchial blocker assembly, having a pair of axial passageways therethrough, is provided which is insertable into and movable along the length of said second flexible tube. One of said axial passageways receives a stylet, said stylet being movable along the length of and rotatable within said axial passageway. Said stylet being sufficiently flexible to guide said endotracheal tube and said bronchial blocker assembly along a pediatric patient's windpipe. Means are provided for fixing said bronchial blocker assembly relative to said second axial passageway when said bronchial blocker assembly is resident therewithin.

25 Claims, 4 Drawing Sheets

U.S. PATENT DOCUMENTS

| | | |
|---|---|---|
| 3,948,255 | 4/1976 | Davidson . |
| 4,022,219 | 5/1977 | Basta . |
| 4,050,466 | 9/1977 | Koerbacher . |
| 4,275,724 | 6/1981 | Behrstock . |
| 4,329,983 | 5/1982 | Fletcher . |
| 4,329,984 | 5/1982 | Kervin . |
| 4,331,143 | 5/1982 | Foster . |
| 4,502,482 | 3/1985 | DeLuccia et al. . |
| 4,582,762 | 4/1986 | Onohara et al. . |
| 4,593,690 | 6/1986 | Sheridan et al. . |
| 4,622,965 | 11/1986 | Teeple . |
| 4,641,646 | 2/1987 | Schultz et al. . |
| 4,655,214 | 4/1987 | Linder . |
| 4,685,457 | 8/1987 | Donenfeld . |
| 4,722,335 | 2/1988 | Vilasi . |
| 4,723,543 | 2/1988 | Beran . |
| 4,727,872 | 3/1988 | Hawk . |
| 4,739,756 | 4/1988 | Horn . |
| 4,774,943 | 10/1988 | Yu . |
| 4,825,858 | 5/1989 | Frankel . |
| 4,825,861 | 5/1989 | Koss . |
| 4,827,925 | 5/1989 | Vilasi . |
| 4,840,172 | 6/1989 | Augustine et al. . |
| 4,840,173 | 6/1989 | Porter, III . |
| 4,850,349 | 7/1989 | Farahany . |
| 4,865,586 | 9/1989 | Hedberg . |
| 4,892,095 | 1/1990 | Nakhgevany . |
| 4,909,248 | 3/1990 | Anderson . |
| 4,955,375 | 9/1990 | Martinez . |
| 4,960,122 | 10/1990 | Mizus . |
| 4,976,261 | 12/1990 | Gluck et al. . |
| 5,005,573 | 4/1991 | Buchanan . |
| 5,009,227 | 4/1991 | Nieuwstad . |
| 5,020,534 | 6/1991 | Pell et al. . |
| 5,033,466 | 7/1991 | Weymuller, Jr. . |
| 5,038,777 | 8/1991 | Dunn . |
| 5,042,476 | 8/1991 | Smith . |
| 5,054,482 | 10/1991 | Bales . |
| 5,056,514 | 10/1991 | DuPont . |
| 5,058,577 | 10/1991 | Six . |
| 5,060,647 | 10/1991 | Alessi . |
| 5,067,497 | 11/1991 | Greear et al. . |
| 5,069,206 | 12/1991 | Crosbie . |
| 5,076,268 | 12/1991 | Weber . |
| 5,076,269 | 12/1991 | Austin . |
| 5,119,811 | 6/1992 | Inglis et al. . |
| 5,143,062 | 9/1992 | Peckham . |
| 5,146,913 | 9/1992 | Khorsandian et al. . |
| 5,146,916 | 9/1992 | Catalani . |
| 5,174,283 | 12/1992 | Parker . |
| 5,201,310 | 4/1993 | Turnbull . |
| 5,203,320 | 4/1993 | Augustine . |

OTHER PUBLICATIONS

"Low Resistance Double–Lumen Endobronchial Tubes", Frank L. Robertshaw, *British Journal of Anaesthesia,* 1962, pp. 576–579.

"The Prevention of Spread During Pulmonary Resection by the Use of a Double–Lumen Catheter", Viking Olov Bjork, M.D. and Eric Carlens, M.D., *Journal of Thoracic Surgery,* vol. 20, 1950, pp. 151–157.

PEDIATRIC ENDOTRACHEAL TUBE WITH BRONCHIAL BLOCKER AND METHOD FOR SELECTIVELY BLOCKING RESPIRATORY AIRFLOW TO A PEDIATRIC PATIENT'S LUNG

FIELD OF THE INVENTION

This invention relates to medicine, specifically to surgery and most particularly to apparatus and methods for selectively blocking respiratory airflow to a pediatric lung or to a single lobe thereof, ancillary to a surgical procedure.

LEXICON

Since this invention relates to surgical procedures and apparatus, this patent application necessarily utilizes terminology from the medical field and from the field of mechanical engineering. To facilitate understanding of this invention by workers in both fields, the following Lexicon is provided; it is to be understood that plurals and variants of these words also have the appropriate meanings indicated in appropriate contexts:

| | |
|---|---|
| Endotracheal tube | A tube insertable into the trachea to provide access to the lungs and other organs. |
| Lumen | The cavity of a tubular member. |

BACKGROUND OF THE INVENTION—DESCRIPTION OF THE PRIOR ART

Endobronchial blockade has been used for single lung ventilation for more than 50 years. An endotracheal tube is positioned within the trachea of a patient. Selective collapse of a targeted lung, or a part thereof, is accomplished by inflating a balloon which is placed on the end of a bronchial blocker protruding from the endotracheal tube thereby restricting airflow to or from the targeted airway.

Use of a single lumen endotracheal tube with a bronchial blocker to allow single lung ventilation soon declined in popularity because it is time consuming and difficult to place the bronchial blocker in position. Moreover, dislodgement of the bronchial blocker is common.

An approach to single lung ventilation described by Inoue et al. (The Journal of Thoracic and Cardiovascular Surgery, Vol. 83, No. 6, pp. 940–41 (1981)) involved the use of an endotracheal tube having a single lumen made of inert silicone. This type of tube, which has come to be called the UNIVENT™ tube (manufactured by Fuji Systems Corporation), has been widely used in adults for both pulmonary and non-pulmonary surgical procedures including operations on the esophagus, the mediastinum and on the ascending and descending aorta. Additionally, the UNIVENT™ tube is used to provide surgical exposure for procedures via thoracoscopy.

Figures 2, 3, 4, 5, 6:
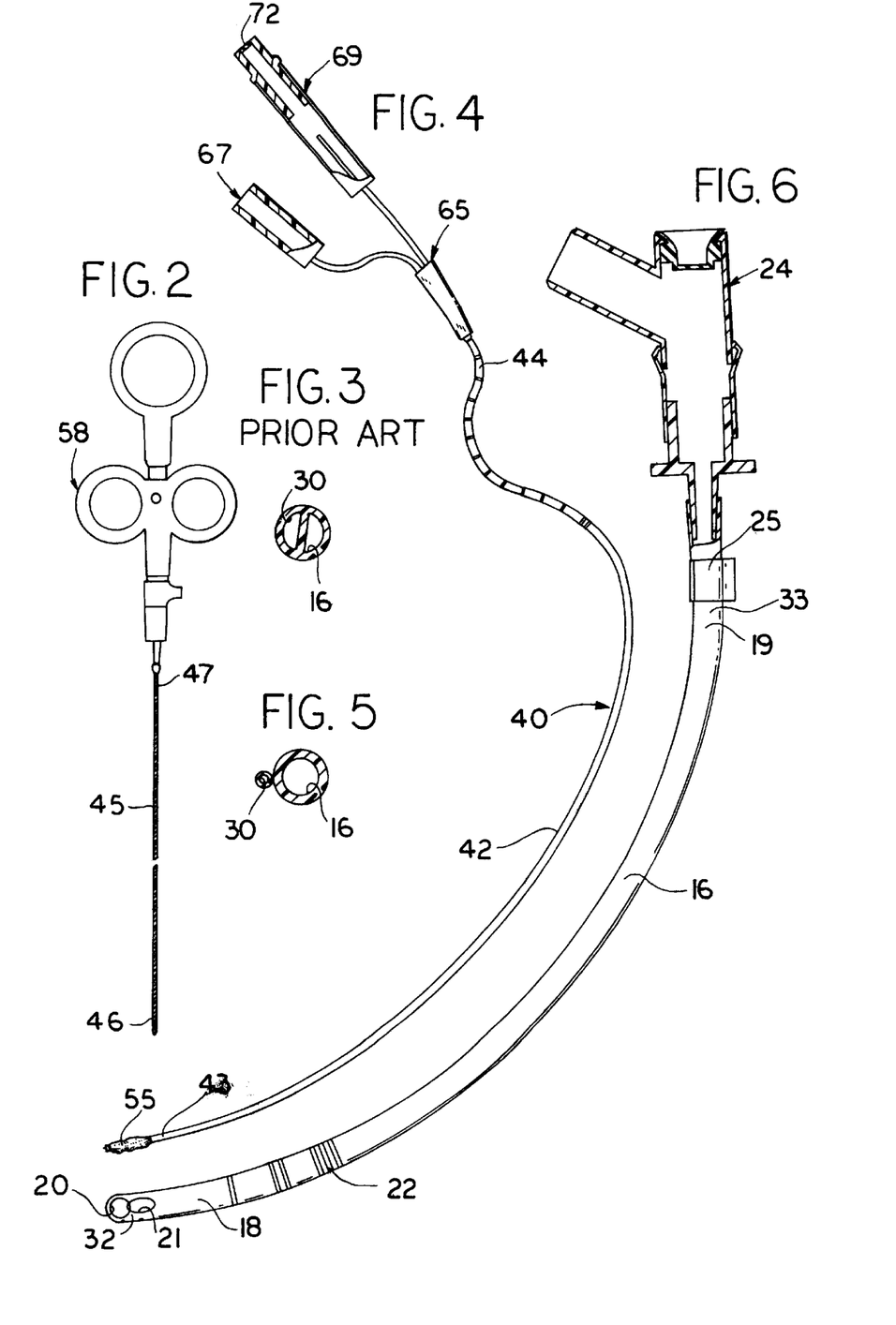
FIG. 2 is a side elevation view of a stylet in accordance with the present invention.
FIG. 3 is an axial sectional view of a prior art double lumen endotracheal tube.
FIG. 4 is a partial sectional view of a bronchial blocker assembly in accordance with the present invention.
FIG. 5 is an axial sectional view of the endotracheal tube and bronchial blocker insertion tube taken along Line 5—5 in FIG. 7 shown with the bronchial blocker assembly removed from within the bronchial blocker insertion tube.
FIG. 6 is a partial sectional view of an endotracheal tube in accordance with the present invention.

Currently, various types of double lumen endotracheal tubes are available for single lung ventilation. A double lumen tube, as shown in FIG. 3, comprises an endotracheal tube with a divider extending axially through the lumen of the tube thereby dividing the lumen into two separate sections. Examples of these types of endotracheal tubes include the Carlens and Robertshaw tubes (*Brit. J. Anaesth.*, Vol. 34, pp. 576–79 (1962) and *Journal of Thoracic Surgery*, Vol. 20, pp. 151–57 (1950)). Early versions of these tubes were made of red rubber, however the modern double lumen endotracheal tube is made of polyvinylchloride.

There are various risks and potential complications attendant to the use of double lumen tubes. Such risks and complications include bronchial and tracheal rupture, traumatic laryngitis, mucosal damage and improper positioning of the tube for the procedure to be performed. Additionally, double lumen tubes are frequently contraindicated in patients presenting a difficult airway and in those patients who are presented for emergency surgery with a full stomach. A further disadvantage attendant to use of double lumen tubes is the need to exchange such double lumen tubes for single lumen tubes upon completion of surgery in those patients requiring post-operative mechanical ventilation. This need arises because double lumen tubes increase resistance to airflow through the tube. Further, due to their necessarily smaller inner diameter, double lumen tubes have an increased risk of becoming plugged with secretions and have a high risk of dislodgement from their proper position within the patient's airway.

The foregoing discussion applies to surgery in general and specifically to adult surgery. When similar procedures are to be used with pediatric patients, additional complications can arise. The smaller size of the pediatric patient makes the margin for error in positioning the tube much smaller.

Heretofore, various methods have been used to achieve lung separation in children. A single lumen tube can normally be passed into either the right main bronchus or the left main bronchus of a pediatric patient. With the single lumen tube approach, reinstitution of two lung ventilation is difficult due to the surgical environment which severely restricts the attending physician's access to the patient's airway. With the single tube approach, when the tube is partially withdrawn in the course of attempting to reinitiate dual lung ventilation, there is a serious risk of removing the tube too far whereupon it can be difficult or impossible to reposition the tube to reinitiate dual lung ventilation. Restarting dual lung ventilation should be accomplished prior to closing the incision.

In some cases, intubation in pediatric patients can be accomplished using fiber optic bronchoscopy. Lung separation has been achieved using a single lumen endotracheal tube and a bronchial blocker such as a FOGARTY™ embolectomy catheter (available from Baxter International, Inc.), a SWAN-GANZ™ catheter (available from Arrow International, Inc.), or a FOLEY™ catheter (also available from Baxter). These methods of lung separation are less than ideal because of the difficulty in maneuvering to achieve exact placement of the blocker and the high risk of dislodgement of the blocker from its optimal position. Further, the known double lumen endotracheal tubes are not practical to use with small children since the small size of the child's trachea would require that each lumen of a double lumen pediatric endotracheal tube be exceedingly small, making the tube prone to clogging with secretions and causing a high resistance to gas flow.

U.S. Pat. Nos. 3,599,642; 3,754,554; 3,948,255; 4,022,219; 4,050,466; 4,275,724; 4,329,983; 4,329,984; 4,331,143; 4,502,482; 4,582,762; 4,593,690; 4,622,965; 4,641,646; 4,655,214; 4,685,457; 4,722,335; 4,723,543; 4,727,872; 4,739,756; 4,774,943; 4,825,858; 4,825,861; 4,827,925; 4,840,172; 4,840,173; 4,850,349; 4,865,586; 4,892,095; 4,909,248; 4,955,375; 4,960,122; 4,976,261; 5,005,573; 5,009,227; 5,020,534; 5,033,466; 5,038,777; 5,042,476; 5,054,482; 5,056,514; 5,058,577; 5,060,647; 5,067,497; 5,069,206; 5,076,268; 5,076,269; 5,119,811; 5,143,062; 5,146,913; 5,146,916; 5,174,283; 5,201,310 and 5,203,320 are prior art which may be relevant to the patentability of this invention.

Additional prior art which may be relevant to the patentability of this invention are the articles "Exsanguinating Hemoptysis" by Garzon, Cerruti and Golding appearing in *The Journal of Thoracic and Cardiovascular Surgery,* Volume 84, pages 829–833, published in 1982; "A New Tube for Single Lung Ventilation" by Karwande, appearing in the October, 1987 issue of the journal *Chest* at pages 761–763; "The Urinary Catheter as a Bronchial Blocker" by Conacher, appearing in the journal *Anaesthesia,* Volume 38, pages 475–477, published in 1983; "Airway Management During Anesthesia for Double-Lung Transplantation Using a Single-Lumen Endotracheal Tube with an Enclosed Bronchial Blocker" by Scheller, Kriett, Smith and Jamieson, appearing in the *Journal of Cardiothoracic and Vascular Anesthesia,* Volume 6, No. 2 published in April of 1992 at pages 204–207; "Lobar Bronchial Blockade in Broncho-Plueral Fistula" by Otruba and Oxorn, published in the *Canadian Journal of Anaesthesia,* Volume 39, No. 2, pages 176–178, published in 1992 and "Use of Fiber Optic Bronchoscope to Assist Placement of a Fogarty Catheter as a Bronchial Blocker" by Oxorn, published in the *Canadian Journal of Anaesthesia,* pages 427–428.

SUMMARY OF THE INVENTION

The problems associated with the known endotracheal tubes and bronchial blockers are solved to a large extent by the apparatus and method of the present invention. The present invention relates to an endotracheal tube with a bronchial blocker insertion tube attached to the outside of the endotracheal tube. By having the bronchial blocker insertion tube attached to the endotracheal tube, the incidence of dislodgement of the bronchial blocker from its optimal position is decreased. Moreover, there is no compromise respective the size of the airway lumen. The apparatus further comprises a flexible stylet which assists the operator in guiding the bronchial blocker selectively into either lung or lobar bronchus. The advantages of the present invention further include the use of an endotracheal tube which is of a single use, disposable variety, which is available in various sizes, and which is easy to insert. Further, since the apparatus of the invention is positionable without extensive trial and error, there is less movement of the apparatus relative to the airway while in place within the airway, which necessarily means the airway experiences less trauma.

In one of its aspects this invention provides an apparatus for selectively blocking respiratory airflow to a pediatric lung or a single lobe thereof. The apparatus includes a flexible, preferably open, endotracheal tube adapted for passage of a flexible fiber optic bronchoscope therethrough. A flexible, preferably open, bronchial blocker insertion tube having an outer diameter less than the endotracheal tube is parallel with and fixedly connected to the endotracheal tube. In one particular embodiment, the endotracheal tube and bronchial blocker insertion tube are integrally formed as a single unit. A bronchial blocker assembly, having first and second axial passageways therethrough, is insertable into and moveable along the length of the bronchial blocker insertion tube.

A stylet is insertable into and moveable along the length of the first axial passageway in the bronchial blocker assembly. The stylet is rotatable within the first axial passageway and is sufficiently flexible to guide the bronchial blocker assembly along a pediatric patient's windpipe by lateral movement of a distal end of the stylet within the bronchial blocker assembly. Movement of the stylet is effectuated by the application of manual force to a second, proximal end of the stylet which extends beyond the end of the first axial passageway and outside of the patient. The apparatus further preferably includes means for axially fixing the bronchial blocker assembly relative to the bronchial blocker insertion tube when the bronchial blocker assembly is resident therewithin.

The bronchial blocker assembly also comprises an inflatable member, such as a cuff or balloon, attached at or near the distal end of the bronchial blocker assembly. The balloon is attached to the bronchial blocker assembly in such a manner that air forced down the second axial passageway of the bronchial blocker assembly inflates the balloon.

In another one of its aspects, this invention provides a method for selectably blocking respiratory airflow through bronchial structure in a pediatric patient's lung or in a single lobe of such a pediatric patient's lung, adjunct to performing a thoracic surgical procedure. The method preferably includes inserting a flexible open-ended endotracheal tube, having a bronchial blocker insertion tube connected thereto and running substantially parallel therewith, through a patient's windpipe. With the endotracheal tube and the bronchial blocker insertion tube in place, a bronchial blocker assembly is inserted sufficiently into the proximal end of the bronchial blocker insertion tube so that the bronchial blocker assembly extends through the bronchial blocker insertion tube and protrudes from the distal end thereof.

A stylet is inserted through a first axial passageway in the bronchial blocker assembly and is maneuvered to position the bronchial blocker assembly at the entrance to an airway which is to be blocked. The stylet is preferably maneuvered from the end thereof proximate the proximal end of the open-ended bronchial blocker insertion tube in order to laterally move the distal end of the stylet and resultantly a distal end of the bronchial blocker assembly. These ends are moved separately from an end of the endotracheal tube which is proximate thereto in order to navigate the tracheal structure as the bronchial blocker insertion tube, having the bronchial blocker assembly resident therewithin, with a stylet in turn being resident within the bronchial blocker assembly, are inserted into the bronchial structure. Thereafter, a balloon or cuff portion of the bronchial blocker assembly is inflated to block a selected passageway or lobe of the pediatric bronchial structure. Desirably, lateral manipulation of the end of the stylet is performed while visually guiding the bronchial blocker assembly within the pediatric tracheal structure using a fiber optic bronchoscope resident within the endotracheal tube.

BRIEF DESCRIPTION OF THE DRAWINGS

The foregoing summary, as well as the following detailed description of the preferred embodiments of the present invention, will be better understood when read in conjunction with the accompanying drawings, in which.

DESCRIPTION OF THE PREFERRED EMBODIMENTS AND BEST MODES KNOWN FOR PRACTICING THE INVENTION

Figure 1:
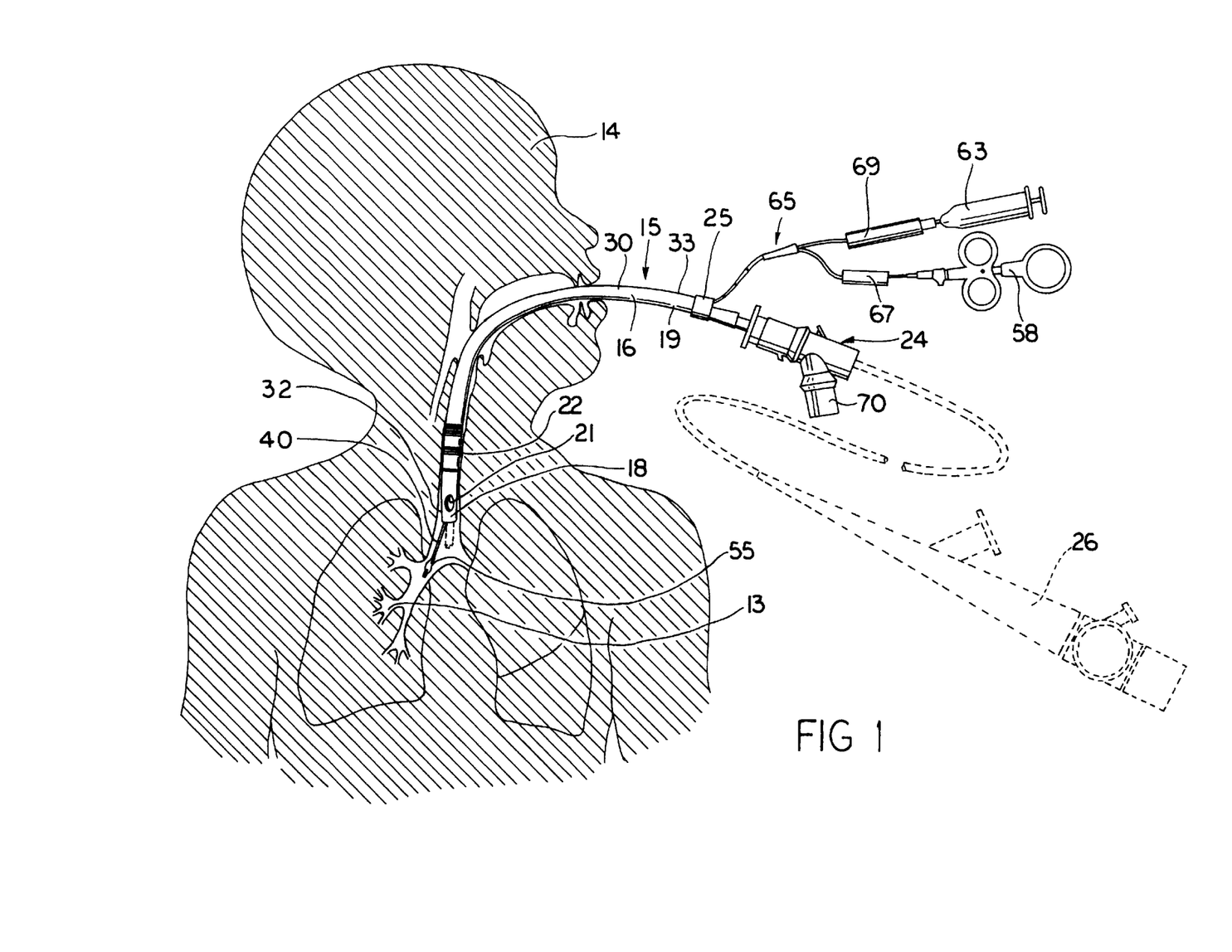
FIG. 1 is an illustration of an apparatus in accordance with the present invention inserted in the trachea of a patient.
Figure 7:
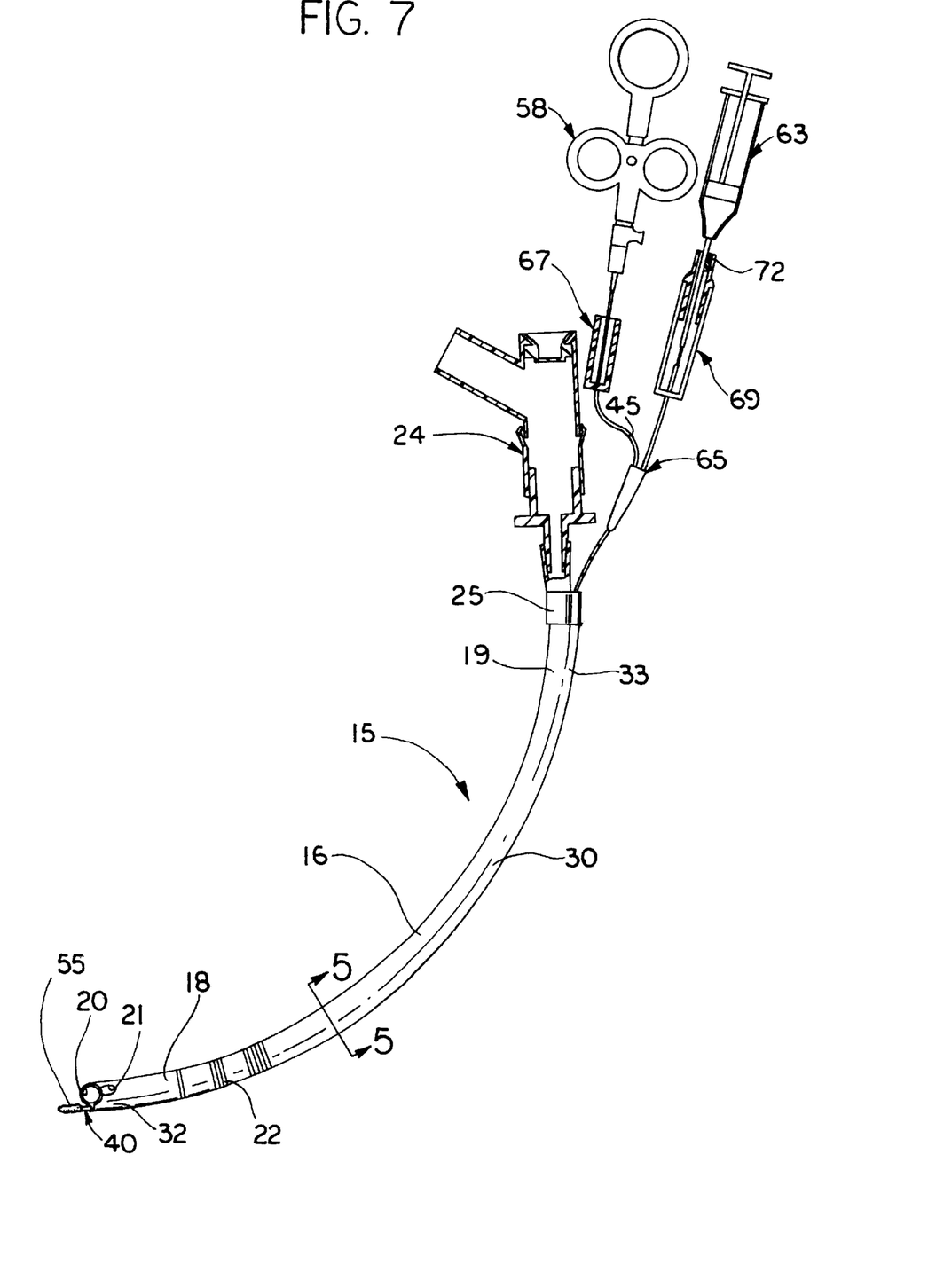
FIG. 7 is a partial sectional view of the apparatus in accordance with the present invention.
Figure 8:
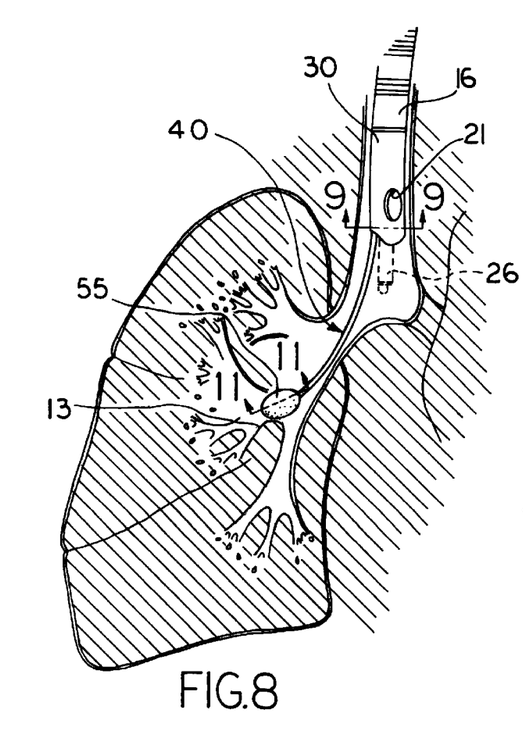
FIG. 8 is an illustration of the distal end of the apparatus in accordance with the present invention positioned within a lobe of a patient's lung.

The present invention generally relates to an apparatus 15, as depicted in FIGS. 1 and 7, for selectively blocking respiratory airflow to a pediatric lung or to a single lobe 13 thereof. The apparatus 15 comprises an endotracheal tube 16 which is adapted to allow for the passage of a bronchoscope 26 therethrough. A bronchial blocker insertion tube 30 is arranged parallel to and fixedly connected with the endotracheal tube 16. The bronchial blocker insertion tube 30 is adapted so that a bronchial blocker assembly 40 is insertable into and slidable within the bronchial blocker insertion tube 30.

Figure 10:
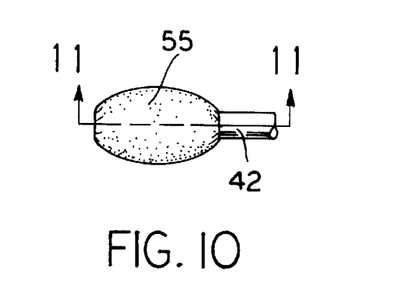
FIG. 10 is an enlarged side elevation view of the cuff.
Figure 11:
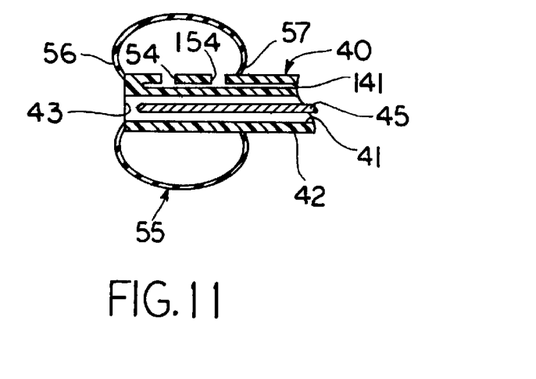
FIG. 11 is a sectional view of the bronchial blocker assembly taken along Line 11—11 in FIG. 8.

As shown in FIGS. 10 and 11, the distal end of the bronchial blocker assembly 40 comprises a flexible tube 42 having two axial passageways, 41 and 141, which extend the length of the bronchial blocker assembly 40. The first axial passageway 41 is adapted to allow for the insertion of a stylet 45 therethrough. The second axial passageway 141 is smaller in diameter than the axial passageway 41 and is adapted to allow air to pass therethrough.

Referring to FIG. 6, the endotracheal tube 16 comprises a length of flexible tube having a distal and a proximal end, 18 and 19 respectively. Preferably the tube is made from a biologically inert plastic such as polyvinylchloride. The outer diameter of the endotracheal tube 16 is sufficiently small to allow the endotracheal tube 16 to be inserted into the trachea of a pediatric patient. However, the inner diameter of the endotracheal tube 16 must be adequately large to allow a bronchoscope 26 to be passed therethrough. Further, the endotracheal tube 16 must be sufficiently long so that the proximal end 19 of the endotracheal tube 16 is extracorporeally accessible when the distal end 18 of the endotracheal tube 16 is in place within the patient's trachea. The dimensions of the endotracheal tube 16 used will therefore vary from patient to patient depending, for example, upon the patient's age and size. Preferably, an endotracheal tube 16 is used having an outer diameter of between about 4.9 and 6.9 mm and an inner diameter of between about 4.0 mm and 5.5 mm. For most patients, an endotracheal tube 16 having a length between about 20 cm and 27 cm is adequate.

The distal end 18 of the endotracheal tube 16 is preferably provided with a beveled end port 20 to enable the endotracheal tube 16 to properly fit at the lower end of the trachea. A Murphy eye 21 is preferably provided in the wall of the endotracheal tube 16 near the distal end 18 of the endotracheal tube 16 to facilitate breathing if beveled end port 20 becomes blocked.

A series of depth markers 22 can be provided along the length of the endotracheal tube 16. When the middle set of lines of depth markers 22 are positioned at the vocal cords of the patient, the endotracheal tube 16 is properly positioned within the patient.

An endotracheal tube fitting or adaptor 24 can be attached near the proximal end 19 of the endotracheal tube 16. The endotracheal tube adaptor 24 is designed to allow the bronchoscope 26 to be easily inserted into the endotracheal tube 16. Additionally, the endotracheal tube adaptor 24 enables the endotracheal tube 16 to be connected to a source of suction when the bronchoscope 26 is not inserted through the adaptor 24 into the endotracheal tube 16. Further, a source of oxygen can be connected to the endotracheal tube 16 through a side port 70 on the adaptor 24. A suitable adaptor 24 is a self-sealing adaptor which allows continuous ventilation through an anesthesia circuit, such as the BODAT Swivel Y (available from Sontek Medical) or the PORTEX™ 65207 adaptor (manufactured by Smiths Industries Medical System, Inc. A clip or fastener 25 is provided to secure the bronchial blocker assembly 40 in position.

Referring to FIGS. 4 and 7, the bronchial blocker insertion tube 30 is comprised of a length of flexible tube having a first and a second end, 32 and 33 respectively. Preferably the tube is made from a biologically inert plastic such as polyvinylchloride. The inner diameter of the bronchial blocker insertion tube 30 must be sufficiently large so that the bronchial blocker assembly 40 can be inserted through and is slidably moveable within the bronchial blocker insertion tube 30. Accordingly, since the bronchial blocker assembly 40 preferably has an outer diameter of between about 1 and about 1.5 mm and an inner diameter of not greater than about 0.5 mm, the bronchial blocker insertion tube 30 must have an inner diameter slightly bigger than the outer diameter of the bronchial blocker assembly 40. The bronchial blocker insertion tube 30 must be long enough so that the second end 33 of the bronchial blocker insertion tube 30 is extracorporeally accessible when the first end 32 of the bronchial blocker insertion tube 30 is in place within the patient 14. Preferably, the bronchial blocker insertion tube 30 is about the same length as the endotracheal tube 16.

Figure 9:
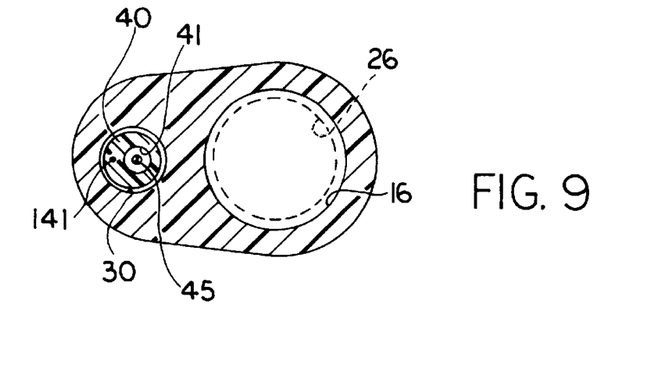
FIG. 9 is a sectional view of the apparatus taken along Line 9—9 in FIG. 8.

The bronchial blocker insertion tube 30 is arranged parallel to and fixedly contacted with the endotracheal tube 16, as best shown in FIG. 5. Preferably the bronchial blocker insertion tube 30 contacts the endotracheal tube 16 over substantially the entire axial length of the endotracheal tube 16. In an even more preferred arrangement as best shown in FIG. 9, the bronchial blocker insertion tube 30 and the endotracheal tube 16 are formed as a unitary member by, for example, extruding the endotracheal tube 16 and the bronchial blocker insertion tube 30 as a single extrusion. In this arrangement, an axial cross section taken through the endotracheal and bronchial blocker insertion tubes, 16 and 30 respectively, is generally in the shape of a figure-eight.

According to the present invention, the apparatus 15 can be supplied in either a right-hand or left-hand model, specifically with the bronchial blocker insertion tube 30 disposed on a selected side of the endotracheal tube 16. A right-hand model is used for surgical procedures involving the right lung and the left-hand model is used for surgical procedures involving the left lung.

Referring again to FIG. 4, the bronchial blocker assembly 40 comprises a length of tubing 42 having a first and a second end, 43 and 44 respectively. The outer diameter of the bronchial blocker assembly 40 is sized so that the bronchial blocker assembly 40 is insertable into and slidably moveable within the bronchial blocker insertion tube 30. The bronchial blocker assembly 40 is longer than the length of the bronchial blocker insertion tube 30, so that the first end 43 of the bronchial blocker assembly 40 can be extended past the first end 32 of the bronchial blocker insertion tube 30 with the second end 44 of the bronchial blocker assembly 40 extending past the second end 33 of the bronchial blocker insertion tube 30. Preferably, the bronchial blocker assembly 40 can be extended about 6 cm past the tip of the endotracheal tube 16.

In the embodiment shown in FIGS. 9 and 11, two axial passageways, 41 and 141, extend from the first end 43 to the second end 44 of the bronchial blocker assembly 40. The first axial passageway 41 is adapted so that a stylet 45 is insertable and rotatable within the first axial passageway 41. The second axial passageway 141 is adapted so that air can pass through the second axial passageway 141.

The bronchial blocker assembly 40 further comprises an inflatable cuff 55 and air vents 54 and 154. The air vents 54 and 154 penetrate the wall of the bronchial blocker assembly 40, near the first end 43 of the bronchial blocker assembly 40, into the axial passageway 141. The cuff 55 comprises a generally cylindrical section of a stretchable material such as silicon having a first end 56 and a second end 57. Both the first end 56 and the second end 57 of the cuff 55 are open. The first end 43 of the bronchial blocker assembly 40 is inserted within the interior of the cuff 55 so that the air vents 54 and 154 are positioned within the interior of the cuff 55. The second end 57 of the cuff is sealed around the bronchial blocker assembly 40 to provide a substantially air-tight seal. The first end 56 of the cuff 55 is also sealed around the bronchial blocker assembly 40 at or near the first end 43 of the bronchial blocker assembly 40, also to provide an air-tight seal. Since the cuff 55 is positioned to cover the air vents 54 and 154, air forced down the axial passageway 141 exits through the air vents 54 and 154 and inflates the cuff 55. Preferably, the cuff 55 has a capacity of between about 1 cc and 2 cc. Preferably, the cuff 55 is positioned such that, when inflated, the cuff 55 at least partially projects over the first end 43 of the bronchial blocker assembly 40 thereby preventing the first end 43 of the bronchial blocker assembly 40 from injuring tissue within the lung or lobe of interest. However, the cuff 55 is positioned in such a manner as to insure that the cuff 55 does not block the first end 43 of the first or larger axial passageway 41 of the bronchial blocker assembly 40. When the cuff 55 is deflated, the first end 43 of the bronchial blocker assembly 40 along with the cuff 55 can be fully retracted within the bronchial blocker insertion tube 30.

Referring to FIG. 2, the stylet 45 comprises a solid or braided wire which is sufficiently flexible to guide the bronchial blocker assembly 40 along a pediatric patient's windpipe by lateral movement of a distal end 46 of the stylet 45 within the axial passageway 41 of the bronchial blocker assembly 40. The stylet 45 is formed of a material which is sufficiently stiff to maintain the stylet 45 in a generally straight configuration but which can be easily flexed. Movement of the stylet 45 is effectuated by the application of manual force to a proximal end 47 of the stylet 45 which extends beyond the second end 44 of the bronchial blocker assembly 40 outside of the patient 14 when the bronchial blocker assembly 40 is residing within and occupying substantially the length of the bronchial blocker insertion tube 30. A deflecting wire hand control 58 is provided to facilitate manipulation of the stylet 45.

The apparatus 15 further includes a clip 25 for axially fixing the bronchial blocker assembly 40 relative to the bronchial blocker insertion tube 30 when the bronchial blocker assembly 40 is resident therewithin, as shown in FIG. 7.

A bronchial blocker adaptor 65 comprising a stylet adaptor can be optionally supplied to facilitate insertion of the stylet 45 into the first axial passageway 41 of the bronchial blocker assembly 40 and to provide a means for connecting the deflecting wire hand control 58 to the stylet 45. Bronchial blocker adaptor 65 can also comprise a syringe adaptor 69 with a pilot balloon so that a syringe 63 can be operatively connected to the bronchial blocker assembly 40 to force air through second axial passageway 141 to inflate balloon 55. The syringe adaptor 69 preferably comprises a valve 72, such as a flap valve, to reversibly seal the syringe adaptor 69 when the syringe 63 is not connected to the bronchial blocker assembly 40.

The present invention also relates to a method for selectively blocking respiratory airflow through bronchial structure in a pediatric patient's lung or in a single lobe of such a pediatric patient's lung. An apparatus 15 in accordance with the present invention is provided. The endotracheal tube 16 along with the bronchial blocker insertion tube 30 are positioned within the patient's trachea. The positioning of the apparatus 15 can be facilitated through the use of a laryngoscope, as would be known to a person skilled in the art. After the endotracheal tube 16 and bronchial blocker insertion tube 30 are properly positioned within the trachea, the endotracheal tube 16 and bronchial blocker insertion tube 30 can be fixed in place with adhesive, as is also known to those skilled in the art. Ventilation via an anesthesia breathing circuit commences after the endotracheal tube is in place.

An appropriately sized bronchoscope 26 is inserted through the endotracheal tube 16. In a preferred embodiment, the bronchoscope 26 is inserted into the endotracheal tube 16 through a self-sealing endotracheal tube adaptor 24 which is attached to end 19 of the endotracheal tube 16.

A bronchial blocker assembly 40 having a cuff or balloon 55 attached at its distal end is then inserted into the bronchial blocker insertion tube 30 so that the first end 43 of the bronchial blocker assembly 40 extends past the first end 32 of the bronchial blocker insertion tube 30. The bronchial blocker assembly 40 is provided with a first axial passageway 41 and a second axial passageway 141.

A stylet 45 is inserted through the first axial passageway 41 so that the distal end 46 of the stylet 45 extends past the first end 43 of the bronchial blocker assembly 40. At this point, the first or distal ends, 43 and 46, of the bronchial blocker assembly 40 and stylet 45 respectively, as well as the balloon 55, are all visible through the bronchoscope 26. The stylet 45 is then used to guide the bronchial blocker assembly 40 so that the balloon 55 at the first end 43 of the bronchial blocker assembly 40 is positioned at the entrance of the airway to be blocked.

Once the balloon 55 has been placed at the desired position, the bronchial blocker assembly 40 is preferably axially fixed relative to the bronchial blocker insertion tube 30 so that the bronchial blocker assembly 40 does not become dislodged. This is preferably accomplished by attaching the bronchial blocker assembly 40 to clip 25. Optimal positioning of the bronchial blocker assembly 40 is accomplished by directly viewing the bronchial blocker assembly 40 through the bronchoscope 26.

The balloon 55 is then inflated by forcing air through the second axial passageway 141. In a preferred embodiment, a syringe 63 is used to force air through the second axial passageway 141.

The apparatus and method of the present invention is particularly applicable for procedures requiring single lung anesthesia such as closed heart procedures, lung transplants, anterior spine fusions, lobectomies, thoroscopies, and other nonpulmonary thoracic surgeries. The present invention is also useful for single lobe exclusion for suppurative disease, localized hemoptysis, foreign bodies wedged in the distal bronchus requiring removal by thoracotomy, tumor resection, or unilateral lung lavage. Further, the present invention can be used for the temporary occlusion of bronchopleural fistula.

While the preferred embodiments of the invention have been described above and alternative embodiments have also been described, the scope of protection to which the invention is believed entitled is defined by the claims and by equivalents thereto which perform substantially the same function in substantially the same way to achieve substantially the same result as set forth in the claims, so long as such substantial equivalents, as defined by one or more claims for such substantial equivalent, do not read on the prior art.

We claim the following:

1. Apparatus for selectively blocking respiratory air flow to a pediatric lung or a single lobe thereof, comprising:
   a. a flexible endotracheal tube adapted for passage of a fiber optic bronchoscope therethrough;
   b. a second flexible tube having an outer diameter less than said endotracheal tube, parallel with and fixedly contacting said endotracheal tube;
   c. a bronchial blocker assembly insertable into and movable along the length of said second flexible tube, having a pair of axial passageways therethrough;
   d. a stylet insertable into and movable along the length of one of said axial passageways in said bronchial blocker assembly, said stylet being rotatable within said axial passageway and sufficiently stiff to maintain the stylet in a generally straight configuration but which is easily flexed to guide said endotracheal tube and said bronchial blocker assembly along a pediatric patient's windpipe by lateral movement of an end of said stylet within said bronchial blocker assembly responsively to manual force applied to a second end of said stylet outside of said bronchial blocker assembly when said bronchial blocker assembly is resident within and occupied substantially the length of said second flexible tube and said stylet is resident within and occupied substantially the length of said bronchial blocker assembly; and
   e. means for axially fixing said bronchial blocker assembly relative to said second axial passageway when said bronchial blocker assembly is resident therewithin.

2. Apparatus of claim 1 wherein said endotracheal tube and said second flexible tube are formed as a unitary member.

3. Apparatus of claim 1 wherein said second flexible tube fixedly contacts said endotracheal tube over the axial length thereof.

4. Apparatus of claim 1 wherein said endotracheal tube and said second flexible tube are a single extrusion.

5. Apparatus of claim 4 wherein there is a continuous bond between said flexible endotracheal tube and said second flexible tube over the axial length of contact therebetween.

6. Apparatus of claim 1 wherein the outer diameter of said endotracheal tube is not more than about 6.9 mm.

7. Apparatus of claim 1 wherein the inner diameter of said endotracheal tube is not more than about 5.5 mm.

8. Apparatus of claim 1 wherein said stylet is braided substantially over the axial length thereof.

9. Apparatus of claim 1 wherein said stylet has a solid cross section.

10. Apparatus of claim 1 wherein the inner diameter of said endotracheal tube is greater than about 4.0 millimeters.

11. Apparatus of claim 1 wherein the inner diameter of said endotracheal tube is between about 4.0 millimeters and about 5.5 millimeters.

12. Apparatus of claim 1 wherein said bronchial blocker assembly includes an expandable cuff.

13. Apparatus of claim 12 wherein said cuff is inflatable.

14. Apparatus of claim 13 wherein said cuff has a capacity of between about 1 and about 2 cubic centimeters.

15. Apparatus of claim 1 wherein a distal end of said endotracheal tube projects distally beyond a distal end of said second flexible tube.

16. Apparatus of claim 1 wherein said endotracheal tube has a beveled, open distal end.

17. Apparatus of claim 1 wherein said endotracheal tube comprises a side port provided in the wall of the endotracheal tube near the distal end of the endotracheal tube.

18. Apparatus of claim 1 wherein said endotracheal tube comprises a series of depth markers along the length of the endotracheal tube.

19. Apparatus of claim 1 wherein the bronchial blocker assembly comprises:
   a. an air vent penetrating into the second axial passageway near a first end of the bronchial blocker assembly and
   b. an inflatable cuff having a first and a second open end, the first end of the inflatable cuff being sealed around the bronchial blocker assembly near the first end of the bronchial blocker assembly and the second end of the inflatable cuff being sealed around the bronchial blocker assembly proximally to the first end of the inflatable cuff so that the inflatable cuff is positioned to cover the air vent.

20. A method for selectively blocking respiratory air flow through tracheal structure to a pediatric patient's lung or a single lobe of such lung, comprising:
   a. inserting a stylet into one of two passageways in a bronchial blocker assembly;
   b. inserting said bronchial blocker assembly, having said stylet resident therewithin, into a flexible open-ended tube having an endotracheal tube connected thereto and running substantially parallel therewith sufficiently so that said bronchial blocker assembly extends through said flexible open-ended tube and protrudes from the distal end thereof;
   c. laterally maneuvering an end of said stylet extending from said bronchial blocker assembly at the end thereof proximate the entrance end of said open-ended tube, to laterally move the distal end of said stylet and resultantly a distal end of said bronchial blocker assembly and said distal end of said second flexible tube together with an end of said endotracheal tube proximate thereto, to navigate said tracheal structure as said endotracheal tube and said flexible tube, having said bronchial blocker assembly resident therewithin and said stylet in turn resident within said bronchial blocker assembly, are inserted into said tracheal structure; and
   d. expanding a cuff portion of said bronchial blocker assembly to obscure a selected passageway or lobe of said tracheal structure.

21. The method of claim 20 wherein said lateral manipulation of said end of said stylet is performed while visually guiding the endotracheal tube and associated equipment within said tracheal structure using a fiber optic bronchoscope resident within said endotracheal tube.

22. The method of claim 20 wherein the step of laterally maneuvering an end of said stylet to navigate said tracheal structure comprises the step of positioning a middle set of lines in a series of depth markers along the length of the endotracheal tube at the vocal cords of the patient to facilitate proper positioning of the endotracheal tube within the patient.

23. Apparatus for selectively blocking respiratory air flow to a pediatric lung or a single lobe thereof, comprising:
 a. a flexible endotracheal tube adapted for passage of a fiber optic bronchoscope therethrough, the endotracheal tube having a beveled, open distal end, the endotracheal tube comprising:
  i. a side port provided in the wall of the endotracheal tube near the distal end of the endotracheal tube and
  ii. a series of depth markers along the length of the endotracheal tube;
 b. an endotracheal tube adaptor attached near a proximal end of the endotracheal tube;
 c. a second flexible tube having an outer diameter less than said endotracheal tube, parallel with and fixedly contacting said endotracheal tube;
 d. a bronchial blocker assembly insertable into and movable along the length of said second flexible tube, the bronchial blocker assembly having a first and a second axial passageway therethrough, the second axial passageway having an inner diameter that is smaller than an inner diameter of said first axial passageway, the bronchial blocker assembly comprising:
  i. an air vent penetrating into the second axial passageway near a first end of the bronchial blocker assembly and
  ii. an inflatable cuff having a first and a second open end, the first end of the inflatable cuff being sealed around the bronchial blocker assembly near the first end of the bronchial blocker assembly and the second end of the inflatable cuff being sealed around the bronchial blocker assembly proximally to the first end of the inflatable cuff so that the inflatable cuff is positioned to cover the air vent;
 e. a bronchial blocker adaptor attached near a proximal end of the bronchial blocker;
 f. a stylet insertable into and movable along the length of said first axial passageway in said bronchial blocker assembly, said stylet being rotatable within said axial passageway and sufficiently flexible to guide said endotracheal tube and said bronchial blocker assembly along a pediatric patient's windpipe by lateral movement of an end of said stylet within said bronchial blocker assembly responsively to manual force applied to a second end of said stylet outside of said bronchial blocker assembly when said bronchial blocker assembly is resident within and occupied substantially the length of said second flexible tube and said stylet is resident within and occupied substantially the length of said bronchial blocker assembly; and
 g. means for axially fixing said bronchial blocker assembly relative to said second axial passageway when said bronchial blocker assembly is resident therewithin.

24. A method for selectively blocking respiratory air flow through tracheal structure to a pediatric patient's lung or a single lobe of such lung, comprising:
 a. inserting a stylet into a first of two passageways in a bronchial blocker assembly;
 b. inserting said bronchial blocker assembly, having said stylet resident therewithin, into a flexible open-ended tube having an endotracheal tube connected thereto and running substantially parallel therewith sufficiently so that said bronchial blocker assembly extends through said flexible open-ended tube and protrudes from the distal end thereof;
 c. laterally maneuvering an end of said stylet extending from said bronchial blocker assembly at the end thereof proximate the entrance end of said open-ended tube, to laterally move the distal end of said stylet and resultantly a distal end of said bronchial blocker assembly and said distal end of said second flexible tube together with an end of said endotracheal tube proximate thereto, to navigate said tracheal structure as said endotracheal tube and said flexible tube, having said bronchial blocker assembly resident therewithin and said stylet in turn resident within said bronchial blocker assembly, are inserted into said tracheal structure; and
 d. expanding a cuff portion of said bronchial blocker assembly to obscure a selected passageway or lobe of said tracheal structure, said cuff portion having a first and a second open end, the first end of the cuff portion being sealed around the bronchial blocker assembly near the distal end of the bronchial blocker assembly and the second end of the cuff portion being sealed around the bronchial blocker assembly proximally to the first end of the cuff portion so that the cuff portion is positioned to cover an air vent, the air vent penetrating into the second passageway of the bronchial blocker near the distal end of the bronchial blocker assembly.

25. The method of claim 24 wherein the step of laterally maneuvering an end of said stylet to navigate said tracheal structure comprises the step of positioning a middle set of lines in a series of depth markers along the length of the endotracheal tube at the vocal cords of the patient to facilitate proper positioning of the endotracheal tube within the patient.

* * * * *